(12) United States Patent
Ruchti et al.

(10) Patent No.: US 6,587,702 B1
(45) Date of Patent: Jul. 1, 2003

(54) CLASSIFICATION AND CHARACTERIZATION OF TISSUE THROUGH FEATURES RELATED TO ADIPOSE TISSUE

(75) Inventors: Timothy L. Ruchti, Gilbert, AZ (US); Kevin H. Hazen, Gilbert, AZ (US); Marcy R. Makarewicz, Tempe, AZ (US); George M. Acosta, Phoenix, AZ (US)

(73) Assignee: Instrumentation Metrics, Inc, Chandler, AZ (US)

( * ) Notice: Subject to any disclaimer, the term of this patent is extended or adjusted under 35 U.S.C. 154(b) by 0 days.

(21) Appl. No.: 09/489,617

(22) Filed: Jan. 21, 2000

Related U.S. Application Data

(63) Continuation-in-part of application No. 09/359,191, filed on Jul. 22, 1999.
(60) Provisional application No. 60/116,883, filed on Jan. 22, 1999.

(51) Int. Cl.[7] .................................................. A61B 5/00
(52) U.S. Cl. ........................ 600/310; 600/306; 600/473
(58) Field of Search ................................ 600/309–310, 600/322–324, 306, 473–475; 356/39–42

(56) References Cited

U.S. PATENT DOCUMENTS

| | | | | |
|---|---|---|---|---|
| 3,877,818 A | * | 4/1975 | Button et al ................. | 356/416 |
| 4,633,087 A | * | 12/1986 | Rosenthal et al. ........... | 250/339 |
| 4,768,516 A | * | 9/1988 | Stoddart et al. ............. | 600/474 |
| 5,014,713 A | * | 5/1991 | Roper et al. ................. | 600/473 |
| 5,022,261 A | * | 6/1991 | Wolfson et al. .............. | 73/149 |
| 5,348,002 A | * | 9/1994 | Caro ............................. | 600/310 |
| 5,348,003 A | | 9/1994 | Caro | |
| 5,754,293 A | * | 5/1998 | Farhadiroushan ........... | 356/478 |
| 5,792,050 A | * | 8/1998 | Alam et al. .................. | 600/310 |
| 5,807,261 A | * | 9/1998 | Benaron et al. ............. | 600/473 |
| 5,822,219 A | * | 10/1998 | Chen et al. ................... | 702/27 |
| 5,945,676 A | | 8/1999 | Khalil et al. ............ | 250/339.12 |
| 6,014,222 A | * | 1/2000 | Borggaard et al. .......... | 356/419 |

FOREIGN PATENT DOCUMENTS

| | | |
|---|---|---|
| WO | 98/27865 | 7/1998 |
| WO | 99/02956 | 1/1999 |

OTHER PUBLICATIONS

Hans Henrick Thodberg, *A Review of Bayesian Neural Networks with an Application to Near Infrared Spectroscopy*; Jan. 1996; IEEE Transactions on Neural Networks, vol 7, No. 1.

John J. Burmeister and Mark A. Arnold; *Evaluation of Measurement Site for Nonivasive Blood Glucose Sensing with Near–Infrared Transmission Spectroscopy*; 1999; Clinical Chemistry.

* cited by examiner

*Primary Examiner*—Kevin Shaver
*Assistant Examiner*—Matthew Kremer
(74) *Attorney, Agent, or Firm*—Michael A. Glenn; Christopher Peil

(57) ABSTRACT

A non-invasive system for characterizing and classifying the state and structure of a tissue sample operates on a near infrared absorbance spectrum of in vivo tissue. A method that uses near-infrared spectral measurements to characterize and classify the state and structure of tissue sampled based on absorbance features related to fat in adipose tissue is provided. Also provided is a method of estimating skin fold thickness. The approach provides information about sources of tissue variability and is therefore useful for establishing the general category of the tissue structure. Categorization of subjects on the basis of the determination is suitable for further spectral analysis and the measurement of biological and chemical compounds, such as blood analytes. The invention further provides a method of estimating percent body fat based on a skin fold thickness estimate. The invention also provides an apparatus for measuring the absorbance spectra coupled with a digital processor for performing the required analyses.

65 Claims, 14 Drawing Sheets

CLASSIFICATION AND CHARACTERIZATION OF TISSUE THROUGH FEATURES RELATED TO ADIPOSE TISSUE

This application is a continuation-in-part of S. Malin, T. Ruchti, *An Intelligent System for Noninvasive Blood Analyte Prediction*, U.S. patent application Ser. No. 09/359,191, filed Jul. 22, 1999, which claims priority from Provisional Patent Application No. 60/116,883, filed Jan. 22, 1999.

BACKGROUND OF THE INVENTION

1. Technical Field

This invention relates to the classification of individuals by features related to tissue properties. More particularly, the invention relates to methods of characterizing the tissue by features related to the absorbance spectrum of fat in adipose tissue, based on near-IR spectral measurements.

2. Discussion of the Prior Art

Near-infrared (NIR) tissue spectroscopy is a promising noninvasive technology that bases measurements on the irradiation of a tissue site with NIR energy in the 700–2500 nm wavelength range. The energy is focused onto an area of the skin and propagates according to the scattering and absorbance properties of the skin tissue. Thus, energy that is reflected by the skin or that is transmitted through the skin and is detected provides information about the tissue volume encountered. Specifically, the attenuation of the light energy at each wavelength is a function of the structural properties and chemical composition of the tissue. Tissue layers, each containing a unique heterogeneous particulate distribution, affect light absorbance through scattering. Chemical components such as water, protein, fat and blood analytes absorb light proportionally to their molar concentration through unique absorbance profiles or signatures. The measurement of tissue properties, characteristics or composition is based on the technique of detecting the magnitude of light attenuation resulting from its respective scattering and/or absorbance properties.

Blood Analyte Prediction

While noninvasive prediction of blood analytes, such as blood glucose concentration, has been pursued through NIR spectroscopy, the reported success and product viability has been limited by the lack of a system for compensating for variations between individuals that produce dramatic changes in the optical properties of the tissue sample. For example, see O. Khalil *Spectroscopic and clinical aspects of non-invasive glucose measurements*, Clin Chem; vol. 45: pp. 165–77 (1999); or J. Roe, B. Smoller, *Bloodless Glucose Measurements*, Critical Reviews in Therapeutic Drug Carrier Systems, vol. 15, no. 3, pp. 199–241, (1998). These variations are related to structural differences in the irradiated tissue sample between individuals and include, for example, the thickness of the dermis, distribution and density of skin collagen and percent body fat. While the absorbance features caused by structural variation are repeatable by subject, over a population of subjects they produce confounding nonlinear spectral variation. See C. Tan, B. Statham, R. Marks and P. Payne. *Skin thickness measurement by pulsed ultrasound: its reproducibility, validation and variability,* British Journal of Dermatology, vol. 106, pp. 657–667, (1982). Also see S. Shuster, M. Black, E. McVitie, *The influence of age and sex on skin thickness, skin collagen and density* British Journal of Dermatology, vol. 93, (1975). See also J. Durnin, M. Rahaman, *The assessment of the amount of fat in the human body from measurements of skin fold thickness,* British Journal of Nutrition, vol. 21, (1967).

Additionally, variations in the subject's physiological state affect the optical properties of tissue layers and compartments over a relatively short period of time. Such variations, for example, may be related to hydration levels, changes in the volume fraction of blood in the tissue, hormonal stimulation, temperature fluctuations and blood hemoglobin levels.

While these structural and state variations are the largest sources of variation in the measured near-infrared absorbance spectra, they are not indicative of blood analyte concentrations. Instead they cause significant nonlinear spectral variation that limits the noninvasive measurement of blood analytes through optically based methods. For example, several reported methods of noninvasive glucose measurement develop calibration models that are specific to an individual over a short period of time. See, K. Hazen, *Glucose determination in biological matrices using near-infrared spectroscopy,* Doctoral Dissertation, University of Iowa, (August 1995). Also see M. Robinson, R. Eaton, D. Haaland, G. Koepp, E. Thomas, B. Stallard and P. Robinson, *Noninvasive glucose monitoring in diabetic patients: a preliminary evaluation,* Clin. Chem, vol. 38/9, pp. 1618–1622, (1992). Also see S. Malin, T. Ruchti, T. Blank, S. Thennadil and S. Monfre, *Noninvasive prediction of glucose by near-infrared diffuse reflectance spectroscopy,* Clin. Chem, vol. 45:9, pp.1651–1658, (1999).

A related application, S. Malin, T. Ruchti, *An Intelligent System For Noninvasive Blood Analyte Prediction,* U.S. patent application Ser. No 09/359,191; filed Jul. 22, 1999, disclosed an apparatus and procedure for substantially reducing this problem, by classifying subjects according to spectral features that are related to the tissue characteristics prior to blood analyte prediction. The extracted features are representative of the actual tissue volume irradiated. The groups or classes are defined on the basis of tissue similarity such that the spectral variation within a class is small compared to the variation between classes. These internally consistent classes are more suitable for multivariate analysis of blood analytes since the largest source of spectral interference is substantially reduced. In this manner, by grouping individuals according to the similarity of spectral characteristics that represents the tissue state and structure, the confounding nonlinear variation described above is reduced and prediction of blood analytes is made more accurate.

The general method of classification relies on the determination of spectral features most indicative of the sampled tissue volume. The magnitude of such features represents an underlying variable, such as the thickness of tissue or level of hydration.

The absorbance of light by adipose tissue in the subdermis, consisting primarily of cells rich in triglycerides, a class of fatty substance, is among the most significant source of spectral variation in noninvasive near-infrared measurements. While adipose tissue profoundly influences the overall measurement, the volume fraction of fluid rich in blood analytes is relatively small compared to that present in other layers of the skin.

The dermis, for example, is richly supplied with a vascular network. At the interface between the dermis and subcutaneous fat is the deep vascular plexus, a collection of vessels that runs parallel to the skin surface. From the deep vascular plexus, blood vessels rise toward the skin surface to another dense parallel collection of vessels called the superficial vascular plexus, located 0.3 mm to 0.6 mm from the skin surface.

Consequently, the capillary beds of the dermis are targeted for irradiation and measurement of blood analytes, since they have a high volume fraction of analytes, such as glucose, that vary in accordance with actual blood concentration, compared to other layers of the skin. On the other hand, the absorbance of light by the constituents of adipose tissue contributes only confounding effects to the measurement of the targeted analyte, yet it represents, second only to the absorbance of water, the largest source of spectral variation. For example, FIG. 1 shows a near-infrared absorbance spectrum measured on a human subject with large absorbance bands 101, 102, 103, marked by arrows, due to fat stored in adipose tissue. The relative absorbance due to the presence of a typical blood analyte in the sampled tissue volume, such as glucose, is approximately three orders of magnitude smaller than the designated fat absorbance bands.

Thus, the absorbance of light by adipose tissue creates two major obstacles to accurate blood analyte determination. First, the total absorbance related to adipose tissue is a large interference and is not indicative of blood analyte concentrations. Compounding this interference is the fact that the varied attenuation of light by adipose tissue is difficult to model due to the complex nature of the diffusely reflected light in layered systems. Second, the measured absorbance of fat by adipose tissue changes in a manner related to the optical properties of the preceding tissue layers, namely, the dermis, epidermis and stratum corneum. For a given light intensity level, the absorbance due to fat in adipose tissue tends to be constant. However, the light incident on the adipose tissue varies as the surrounding tissue changes according to its physiological state. Thus, the magnitude of fat absorbance in the tissue volume sampled is indirectly related to these changes due to physiological state fluctuations.

Therefore, features related to the absorbance of fat in adipose tissue can be used to classify the nature of the tissue volume sampled with a near-infrared measurement device. The classification of subjects according to the similarity of such features leads to a greater homogeneity of the sampled tissue volume and a reduction in interference related to the skin tissue. This inevitably produces a superior measurement of the concentration of biological compounds in skin, such as blood analytes, among the sub-groups.

Body Composition Estimation

Body composition is an important indicator of health status, and body composition determination plays an important role in health risk assessment and diagnosis, and in monitoring of physical training programs. (See. V. Heyward, L. Stolarczyk, *Applied Body Composition Assessment*, Champaign, Ill.: Human Kinetics, (1996)). Obesity, for example, is a serious health problem that reduces life expectancy by increasing one's risk of developing coronary artery disease, hypertension, Type II diabetes, obstructive pulmonary disease, osteoarthritis and certain types of cancer. The increased health risks associated with obesity are related to the total amount of body fat. Not surprisingly, a large number of methods for estimating body composition exist, many of them based on indirect measurements; for example, hydrostatic weighing, bioelectrical impedance, skin fold measurements and others (See V. Heyward, L. Stolarczyk, *Applied Body Composition Assessment*, Champaign, Ill.: Human Kinetics, (1996)). In addition, near-infrared analysis in the wavelength range 700–1100 nm has been applied to the noninvasive measurement of body fat (See J. Conway, K. Norris, C. Bodwell, *A new approach for the estimation of body composition: infrared interactance*, The American Journal of Clinical Nutrition, pp. 1123–1130, (December 1985).

R. D. Rosenthal in *Near infrared apparatus and method for determining percent fat in a body*, U.S. Pat. No. 4,850,365, issued Jul. 25, 1989 and again in *Near-infrared apparatus and method for determining percent fat in a body*, U.S. Pat. No. 4,928,014 issued May 22, 1990; and A. Roper and K. Johnson, in *Method and apparatus for measuring thickness of fat using infrared light*, U.S. Pat. No. 5,014,713, issued May 14, 1991, disclose methods of performing near-infrared analysis in the 700–1100 nm wavelength regions for the purpose of body composition analysis including the determination of the percent fat and the thickness of fat.

The use of near-infrared analysis has the advantage of being strictly noninvasive, convenient and affordable. The reported methods are similar and generally involve the irradiation of the tissue with near-infrared light at several wavelengths in the 740–1100 nm range and detecting the light absorbed at a multiplicity of wavelengths. A model is constructed for predicting the percent body fat or the thickness of the subcutaneous fat layer on the basis of the measurement, given reference values from an alternate technique of body composition assessment. Conway, for example, used the second derivative of the absorbance spectrum at 916 nm and 1026 nm to estimate the percent fat of several individuals.

Rosenthal reports two similar methods for determining percent fat in a body through the use of the measured absorbance at one wavelength and one bandwidth, respectively, and a mathematical model relating the percent body fat to the absorbance measurement. In addition, data on a plurality of physical parameters of the body, such as height, weight, exercise level, sex, race, waste-to-hip measurement and arm circumference, are proposed for use along with the measured near-infrared absorbance in the quantitative determine of body fat content.

Roper et al. determine the fat thickness in the body through a measuring device involving a pair of infrared emitting diodes and a detector array. A variety of wavelengths in the 700–1100 nm range are detected by the array and produce signals proportional to the light intensity transmitted from the body. These signals are summed and amplified forming a composite signal. The amplitude of this composite signal is claimed to be indicative of the thickness of the layer of fat.

While the reported methods of near-infrared analysis offer some advantage, their utility is significantly compromised due to the wavelength region selected for analysis. It is well understood that melanin is a significant absorber of light below 1100 nm (See R. Anderson, J. Parrish, *The optics of human skin*, J. of Investigative Dermatology, vol. 77 (1), pp. 13–19, (1981). Therefore, skin color causes large spectral variation at wavelengths below 1100 nm and represents a major confounding effect and source of bias. Furthermore, the depth of penetration in this wavelength region far exceeds the depth of subcutaneously stored fat. In addition, the potential interference due to visible light in this wavelength region is well known and requires special measurement equipment and requirements for blocking it. A method for determining the thickness of subcutaneous fat and percent body fat through the use of near-infrared energy at higher wavelengths (1100–2500) nm would clearly be advantageous. In this range the depth of penetration is limited to subcutaneous tissue. The optical properties of the adipose cells, as manifested in the measured absorbance spectrum, can be used to estimate the thickness of the subcutaneous tissue and overall level of fatness of the individual.

SUMMARY OF THE INVENTION

The invention provides a novel apparatus and related procedures for determination of features related to the absorbance of fat in adipose tissue and subsequent classification of subjects prior to blood analyte estimation. A method is provided for determining the thickness of subcutaneous fat and percent body fat through the use of near-infrared energy at longer wavelengths in the spectral region of 1100–2500 nm. In this range the depth of penetration is limited to subcutaneous tissue. The optical properties of the adipose cells, as manifested in the measured absorbance spectrum, can be used to estimate the thickness of the subcutaneous tissue and overall level of fatness of the individual without interference from deeper tissue layers or skin pigmentation.

In general, the apparatus includes an energy source, a wavelength separator, an optical interface to the subject, a sensor element, and an analyzer. The general method of the invention includes the steps of measuring the NIR absorbance spectra of an in vivo tissue sample; detecting outliers, invalid measurements related to various sources of error; subjecting the measured spectrum to various pre-processing techniques; feature extraction, in which the spectral features specifically related to absorbance of fat in adipose tissue are identified and isolated; and calibration, in which the extracted features are compared to a calibration set of exemplary measurements to characterize the spectrum for further blood analyte prediction. A skin fold thickness estimate may be made, and a subsequent estimate of percent body fat.

These and other features, aspects and advantages of the invention will be better understood with reference to the following description, drawings and appended claims.

DETAILED DESCRIPTION

Figure 1:
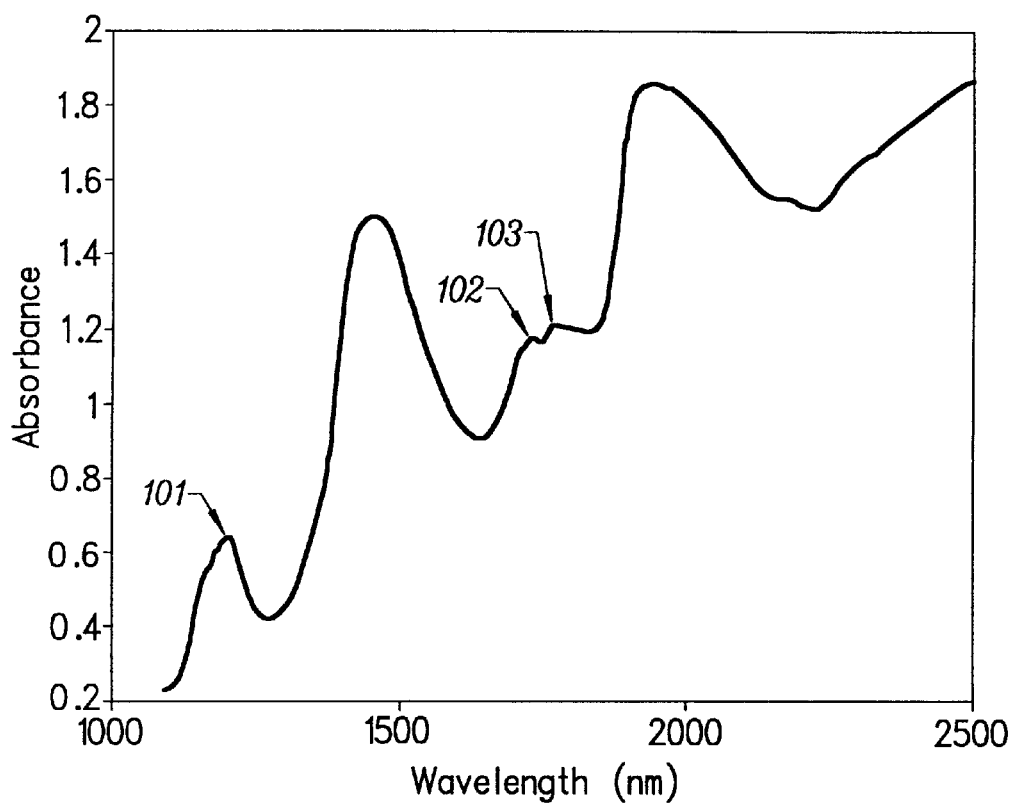
FIG. 1 is a plot of a near-IR absorbance spectrum measured on a human subject showing absorbance bands due to fat stored in adipose tissue.

A system for non-invasively determining features related to the absorbance of adipose tissue provides an apparatus for measuring the infrared absorbance by tissue irradiated with near-infrared energy and procedures for extracting and classifying the tissue characteristics. Alternately, the absorbance spectrum measured is processed and subjected to an estimation procedure for determining the skin fold thickness and/or the percent body fat.

APPARATUS

The apparatus includes an energy source 21, a sensor element 26, an optical interface to the subject 25, a wavelength selection device 22 and an analyzer 33. The energy source 21 generates near-infrared energy in the wavelength range 1100–2500 nm and may consist of a device such as an LED array or a quartz halogen lamp. The sensing elements 26 are detectors that are responsive to the targeted wavelengths. The wavelength separation device 22 may be a monochromator, or an interferometer. Wavelength separation may also be achieved through successive illumination of the elements of the previously described LED array. The optical interface 25 to the subject 20 includes a means for transmitting energy 23 from the source 21 to the target skin tissue measurement site and may be, for example, a light pipe, fiber-optic probes, a lens system or a light directing mirror system. The optical interface 25 to the subject also includes a means for collecting energy 24 from the surrounding tissue areas in reflectance mode at an optimally determined distance(s) and may be composed of staring detectors or fiber optic probes. The collected light is converted to a voltage 26 and sampled through an analog-to-digital converter 27 for analysis on a microprocessor based system 33.

Figure 2:
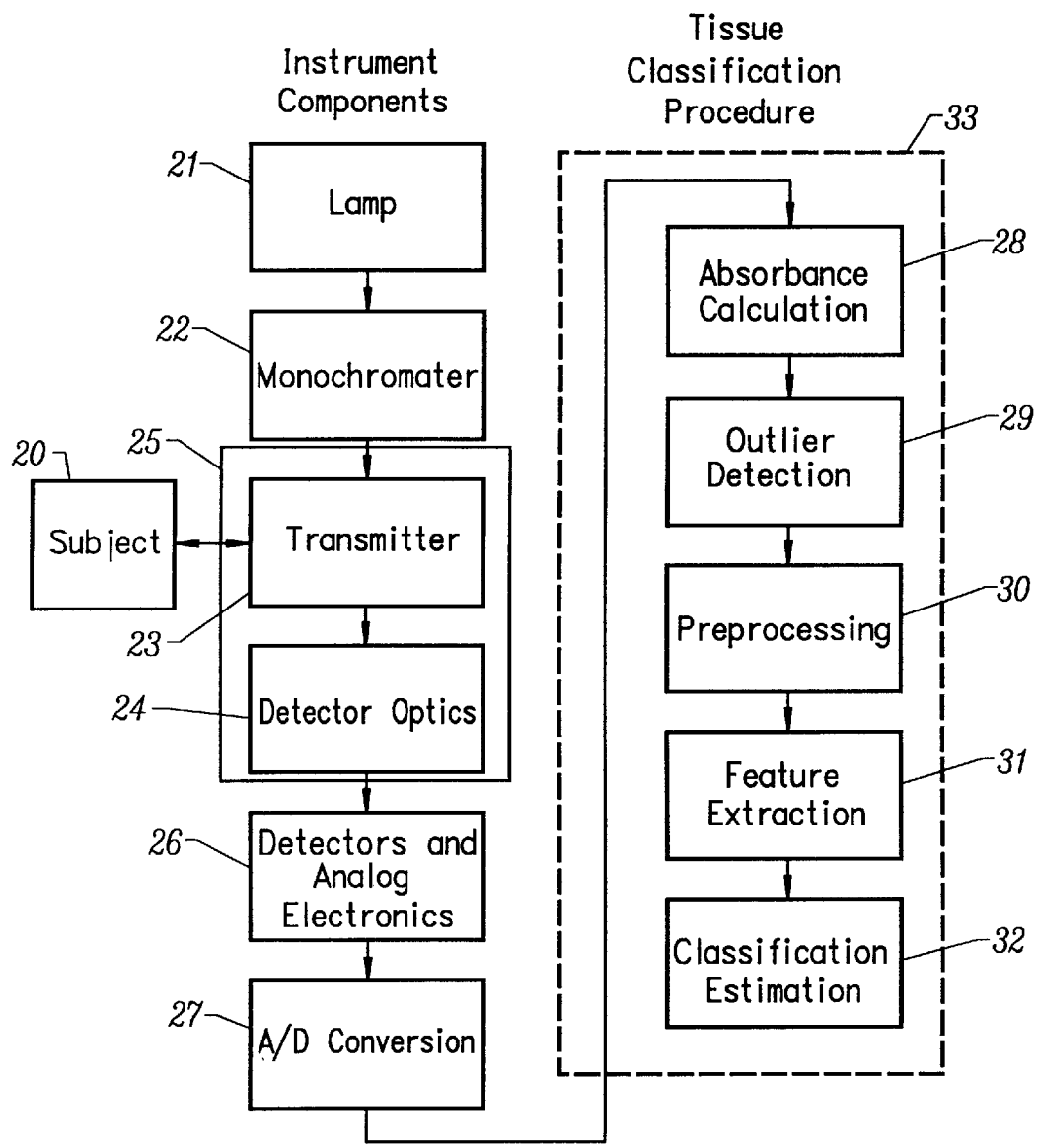
FIG. 2 is a block diagram of a system for classifying tissue according to features related to the absorbance spectra of body fat according to the invention.

In the preferred embodiment, the instrument employs a quartz halogen lamp 21, a monochromator 22 and InGaAs detectors 26. The detected intensity from the sample is converted to a voltage through analog electronics 26 and digitized through a 16-bit A/D converter 27. The spectrum is passed to a processor 33 for processing through the classification procedure. First, the absorbance is calculated 28 on the basis of the detected light through $-\log(R/R_0)$ where R is the reflected light and $R_0$ is the light incident on the sample determined by scanning a reference standard. Subsequent processing steps, described below, result in either a classification 32 or a message indicating an invalid measurement. A block diagram of the integrated system is shown in FIG. 2.

In an alternative embodiment, a group of LED's is employed as an energy source 21 to produce energy at pre-selected wavelengths, which is subsequently transmitted 23 toward the skin. The LED's, which surround a single detection element 26 radially, are alternately energized, and the detected energy from each LED that is reflected by or transmitted through the skin is used to form one spectrum. The edge-to-edge distance between each of the LED's and the detector element, or the distance between the point of illumination and the point of detection, is specific to the wavelength of the energy being emitted from the respective LED's. The preferred distance from the point of illumination, comprising the light-emitting surface of the LED's, and the point of detection is a minimum of 1 mm and maximum of 3 mm. The 1 mm distance is used for wavelengths above 1380 nm and the 3 mm distance for wavelengths in the region 1100–1380 nm. The set of wavelengths includes but is not limited to 1100, 1208, 1210, 1275, 1350, 1650, 1720, 1760 nm. The illumination and detection elements 21, 26 are coupled to the target site through staring optics and a lens system 23, 24. One skilled in the art will appreciate that other coupling methods are also applicable, including fiber optics, with the particular configuration being dictated by the desired distance between the points of illumination and detection.

Alternatively, the measurement can be accomplished with existing commercially available NIR spectrometers, including a Perstorp Analytical NIRS 5000 spectrometer or a Nicolet Magna-IR 760 spectrometer. In addition, the measurement can be made by collecting reflected light off the surface of the skin or light transmitted through a portion of the skin, such as the finger or the ear lobe. Further, the use of reflectance, transmittance, or transreflectance can replace the preferred absorbance measurement.

GENERAL PROCESSING PROCEDURE

The general procedure for determination of features related to the absorbance of triglycerides in adipose tissue is implemented in a microprocessor 33 that automatically receives the measurement information from the ADC 27 as depicted in FIG. 2. Subsequent to the calculation of an absorbance spectrum 28, the main components of the feature extraction and classification and/or estimation procedures include outlier detection 29, preprocessing 30, feature extraction 31 and classification and/or estimation 32. The design of each procedure is performed on the basis of a calibration set of exemplary measurements. In this section we summarize the general steps that are described in detail in the subsequent Implementation Section.

Measurement

The measurement 28 is a spectrum denoted by the vector $m \in R^N$ of absorbance values pertaining to a set of N wavelengths $\lambda \in R^N$ that span the near infrared (1100 to 2500 nm). The spectrum is calculated thusly the detected light is used to create a graph of $-\log R/R_s$, where R is the reflectance spectrum of the skin and $R_s$ is the reflectance of the instrument standard. In infrared spectroscopy, this graph is analogous to an absorbance spectrum containing quantitative information that is based on the known interaction of the incident light with components of the body tissue and will be henceforth referred to in this manner. A plot of m versus $\lambda$ is shown in FIG. 1. More particularly, however, the measurement can consist of a specific selection of wavelengths in the near infrared that have been optimized for the extraction of features related to the absorbance of fat as described further below.

Outlier Detection

The outlier detection procedure 29 is a method of detecting invalid measurements through spectral variations that result from problems in the instrument, poor sampling of the subject or a subject outside the calibration set. The preferred method for the detection of spectral outliers is through a principal component analysis and an analysis of the residuals. First, the spectrum, m, is projected onto five eigenvectors, contained in the matrix o, that were previously developed through a principal component analysis on a calibration set of exemplary absorbance spectra and are stored by the computer system that houses the processor 33. The calculation is given by $$xpc_o = \sum_{k=1}^{7} mo_k \qquad (1)$$

and produces the 1 by 5 vector of scores, $xpc_o$ where $o_k$ is the $k^{th}$ column of the matrix o. The residual, q, is determined according to $$q = m - xpc_o o^T \qquad (2)$$

and compared to three times the standard deviation of the expected residual of the calibration set. If greater, the sample is reported to be an outlier and the procedure is terminated.

Preprocessing

Preprocessing 30 includes operations such as wavelength selection, scaling, normalization, smoothing, derivatives, filtering and other transformations that attenuate noise and instrumental variation without adversely affecting the signal of interest. The preprocessed measurement, $x \in R^N$, is determined according to $$x = h(\lambda, m) \qquad (3)$$

where $h:R^{N \times 2} \to R^N$ is the preprocessing function. Wavelength selection is performed on the data to eliminate extraneous variables that may bias the calibration or portions of the measured spectrum with a low signal-to-noise ratio. The specific methods used for feature extraction and estimation of skin fold thickness, described in more detail in the Implementation Section, include wavelength selection, multiplicative scatter correction and derivatives (See P. Geladi, D. McDougall, H. Martens, *Linearization and Scatter-Correction for Near-Infrared Reflectance Spectra of Meat,* Applied Spectroscopy, vol. 39: pp. 491–500, (1985). Also see A. Savitzky, M. Golay, *Smoothing and Differentiation of Data by Simplified Least Squares Procedures,* Anal. Chem., vol. 36, no. 8, pp. 1627–1639, (1964).

Feature Extraction

Feature extraction 31 determines the salient characteristics of measurements that are related to the absorbance of triglycerides in adipose tissue. The magnitude of a particular feature, is specific to the volume of adipose tissue irradiated by the light. The measured characteristics of this tissue volume are dependent upon the optical properties of the preceding tissue layers and the optical properties of the adipose tissue. Examination of features from different wavelength regions can be used to provide information about the characteristics of the dermis and properties of the adipose tissue.

In general, feature extraction is any mathematical transformation that enhances a quality or aspect of the sample measurement for interpretation. The purpose of feature extraction is to represent concisely and to enhance the properties and characteristics of the tissue measurement site for skin fold thickness estimates, classification and body fat percent measurement. In addition, the features provide significant information about the tissue properties they represent and can be used for alternate purposes such as system diagnostics or optimization.

The features are represented in a vector, $z \in R^M$ that is determined from the preprocessed measurement through $$z = f(\lambda, x) \quad (4)$$

where $f: R^N \to R^M$ is a mapping from the measurement space to the feature space. Decomposing f(.) will yield specific transformations, $f_i(.): R^N \to R^{M_i}$, for determining a specific feature. The dimension, $M_i$, indicates whether the $i^{th}$ feature is a scalar or a vector and the aggregation of all features is the vector z. When a feature is represented as a vector or a pattern, it exhibits a certain structure indicative of an underlying physical phenomenon.

The individual features are divided into two categories:

abstract, and simple.

Abstract features do not necessarily have a specific interpretation related to the physical system. Specifically, the scores of a principal component analysis are useful features although their physical interpretation is not always known. For example, the principal component analysis, provides information regarding the nature of the tissue absorbance spectrum. The most significant tissue variation is generally related to its structure, and the absorbance of adipose tissue is an indicator of variation in the structure of the preceding tissue layers. Therefore, the scores of the principal component analysis provide useful information for classification on the basis of the optical properties of the adipose tissue and constitute a valuable set of features.

Simple features are derived from an a priori understanding of the sample and can be related directly to a physical phenomenon. For example, the thickness of the dermis or subcutaneous layer results in specific spectral manifestations. These spectral variations are extracted and enhanced and serve as both a feature for subject classification and a measurement of their respective tissue properties.

In the general case the full spectrum can be passed to the classification system. However, the following three specific methods of feature extraction, which have been shown to provide superior classification performance and measurement of other relevant tissue properties are described further below:

The scores from factor analysis, specifically principal component analysis.

Relative absorbance of water and fat.

Normalized magnitude of the absorbance bands of triglycerides in adipose tissue

The detailed implementation of these approaches for extracting features on the basis of a calibration set is provided in the next section.

Calibration

The preprocessed spectra and/or the extracted features are subjected to one of two further processing steps. First, decisions may be made regarding the extracted features for the purpose of subject classification. The determination of a change in the state of the dermis may be made on the basis of the extracted feature through a method of classification 32, for example the degree of tissue hydration. Alternately, the subject may be classified as fat because the sampled tissue volume produced a significant feature related to the absorbance of fat. Similarly, the subject may be classified as thin because the feature related to the absorbance of fat has a small magnitude. In either case, the classification is based on an assessment of the tissue volume sampled and not the overall body composition of the individual.

The preprocessed spectrum may subjected to an estimation 32 algorithm that estimates the thickness of the adipose layer or the percent body fat of the subject. In the case of skin fold thickness estimation, the estimation procedure is relatively simple and can operate on the basis of a preprocessed spectrum or extracted features.

In the case of the body composition determination, the procedure relies on the implementation of a model that maps the absorbance spectrum to a percent body fat determination. Although salient features may be used in this algorithm the overall body composition is dependent upon other characteristics, in addition to the local thickness of the adipose tissue. Demographics, such as age and sex, play an important role in the determination of body fat (See Heyward, et al., op. cit.]. Both age and sex can be estimated from the same measured spectrum as previously disclosed in two related patent applications, T. Ruchti, S. Thennadil, S. Malin, J. Rennert *A System For The Non-Invasive Estimation Of Relative Age,* U.S. patent application Ser. No, 09/487,236, filed on Jan. 19, 2000 and T. Ruchti, S. Thennadil, S. Malin and J. Rennert, *Classification For Sex Discrimination And Tissue Characterization,* U.S. patent application Ser. No. 09/487,733, filed on Jan. 19, 2000. Therefore, the method for body composition assessment utilizes both the age and sex determination procedures previously described and the skin fold thickness estimation method disclosed herein.

Crisp Classification

The classification of the subject on the basis of the extracted features is performed through a classification step that involves a mapping and a decision. The mapping step is given by $$L = f(z) \quad (5)$$

where L is a scalar that can be used to measure the distance from the predefined body composition categories. For example, two values, $L_{lean}$ and $L_{fat}$, associated with the representative or mean value of L for a lean and a fat category respectively are predefined and the class assignment is based on the closeness of L to $L_{lean}$ and $L_{fat}$. For example, the distance of L to a previously established class means that classes can be measured by $$d_{lean} = |L_{lean} - L|$$

$$d_{fat} = |L_{fat} - L|. \quad (6)$$

The decision is made as follows:

if $d_{lean} < d_{fat}$ then the tissue volume sampled is classified as lean or containing relatively low percentage amount of trigylcerides.

if $d_{lean} > d_{fat}$ then the tissue volume sampled contains a relatively high amount of triglycerides and is classified as fat.

The mapping and decision limits are determined from a calibration set of exemplary features and corresponding assessments of reference values, i.e. lean or fat, through a classification calibration procedure. Existing methods include linear discriminant analysis, SIMCA, k nearest-neighbor, fuzzy classification and various forms of artificial neural networks. Furthermore, one skilled in the art will appreciate that more than two distinct classes for fat can be defined with an upper limit based on the accuracy of the measurement device. (See R. Duda, P. Hart, *Pattern Classification and Scene Analysis,* John Wiley and Sons, New York (1973); S. Wold, M. Sjostrom, *SIMCA: A method for analyzing chemical data in terms of similarity and analogy,* Chemometrics: Theory and Application, ed. B. Kowalski, ACS Symposium Series, vol. 52, (1977); J. Bezdek, S. Pal, eds. *Fuzzy Models for Pattern Recognition,* IEEE Press, Piscataway, N.J., (1992); J. Keller, M. Gray, J. Givens. *A Fuzzy K nearest Neighbor Algorithm,* IEEE Transactions on Systems, Man, and Cybernetics, Vol. SMC-15, vol. 4, pp. 580–585, (July/August, 1985); Y. Pao, *Adaptive Pattern Recognition and Neural Networks,* Addison-Wesley Publishing Company, Inc., Reading, Mass., (1989).

Fuzzy Classification

While statistically based class definitions provide a set of mutually exclusive classes, the appropriate classification of a tissue sample and the resulting spectral variation change over a continuum of values. For example, the level of leanness of a sampled tissue volume varies within a population of individuals in a continuous rather than discrete manner. Therefore, the natural variation in the spectra results in significant class overlap. Distinct class boundaries based on the absorbance of fat in adipose tissue do not exist and many measurements are likely to fall between classes and have a statistically equal chance of membership in any of several classes. Therefore, hard class boundaries and mutually exclusive membership functions may be inadequate to model the variation encountered in the target population.

A more versatile method of class assignment is based on fuzzy set theory (See J. Bezdek, et al., *Fuzzy Models for Pattern Recognition,* IEEE Press, Piscataway, N.J., (1992); C. Chen, ed., *Fuzzy Logic and Neural Network Handbook,:* IEEE Press, Piscataway, N.J. (1996); L. Zadeh, *Fuzzy Sets,* Inform, Control, vol. 8, pp. 338–353, (1965). Generally, membership in fuzzy sets is defined by a continuum of grades and a set of membership functions that map the feature space into the interval [0,1] for each class. The assigned membership grade represents the degree of class membership with "1" corresponding to the highest degree. Therefore, a sample can simultaneously be a member of more than one class.

The mapping from feature space to a vector of class memberships is given by $$c_k = f_k(z) \tag{7}$$

where k=1,2, . . . P, $f_k(.)$ is the membership function of the $k^{th}$ class, $c_k \in [0,1]$ for all k and the vector $c \in R^P$ is the set of class memberships. An example of the general equation employed to represent a membership function is $$y = e^{\frac{-1}{2\sigma^2}(z-\bar{z})^2}$$

where y is the degree of membership in a sub-set, z is the feature used to determine membership, $\bar{z}$ is the mean, or center of the fuzzy sub-set and $\sigma$ is the standard deviation. However, one skilled in the art will appreciate that the suitable membership function is specific to the application.

The membership vector provides the degree of membership in each of the predefined classes and can be used for blood analyte prediction as disclosed by Malin, et. al. in a related application, U.S. patent application Ser. No. 09/359, 191, previously cited. Alternately, the degree of class membership can be used to calculate the thickness of adipose tissue and the body composition of the individual through a suitable defuzzification function. The defuzzification function can be determined as described by S. Malin, T. Ruchti, *An Intelligent System For Noninvasive Blood Analyte Prediction,* U.S. patent application Ser. No 09/359,191; filed Jul. 22, 1999. Alternately a calibration set of exemplary spectral measurements and associated reference values can be used to determine a calibration model for mapping the class membership to an estimate of the selected variable, skin fold thickness or body composition, for example.

Estimation

The method of estimation relies on the employment of a calibration model that maps the preprocessed spectrum through a linear or nonlinear mapping to an estimate of a target variable, such as skin fold thickness or percent body fat. In the linear case, given the processed spectrum, x, and the calibration model coefficients $w_c$ the estimate is determined according to $$\hat{y} = \sum_{k=1}^{N} w_{c,k} x_k \tag{9}$$

were $w_{c,k}$ is the $k^{th}$ element of $w_c$ and $\hat{y}$ is the estimated variable. One skilled in the art will appreciate that a nonlinear mapping from x to $\hat{y}$ can also be easily specified through artificial neural networks, nonlinear partial-least squares regression or other nonlinear method of calibration (See P. Geladi, B. Kowalski, *Partial least-squares regression: a tutorial,* Analytica Chimica Acta, vol. 185, pp. 1–17, (1986); Y. Pao, *Adaptive Pattern Recognition and Neural Networks,* Addison-Wesley Publishing Company, Inc., Reading, Mass., (1989).

The preferred model is linear and is constructed through a factor analysis to decompose the high dimensional, or redundant, data consisting of absorbance, intensity or reflectance measurements at several hundred wavelengths to a few significant factors that represent the majority of the variation within the data set. The factors that capture variation in the spectra correlated to the target variable are used in the calibration model and the samples are projected into the resulting factor space to produce a set of scores for each sample. Finally, multiple linear regression is applied to model the relationship between the scores of the significant factors and the target variable.

In the case of body composition determination, the near-IR age estimate and the near-IR sex estimate for the subject are used with the near-IR estimate of skin fold thickness. Two procedures for body composition determination are disclosed herein. The first employs different calibrations for mapping skin fold thickness to percent body fat for each age group and each sex. The second and preferred implementation is a model that maps the three variables skin fold thickness, age and sex to an estimate of the percent body fat of the individual. This mapping is of the form $$y = f(x_1, x_2, x_3) \tag{10}$$

where y is the estimate of the percent body fat, $x_1$ is the near-IR estimate of skin fold thickness, $x_2$ is the near-IR estimate of the sex and $x_3$ is the near-IR estimate of the age as previously disclosed in the two related applications Ser. Nos. 09/487,236 and 09/487,236. The model f( ) is determined by applying an analytical technique such as artificial neural networks to a calibration set of exemplary measurements. One skilled in the art will appreciate that other methods of nonlinear regression can be applied to determine alternate forms for f( ).

IMPLEMENTATION DETAILS

Basis Set

Figure 3:
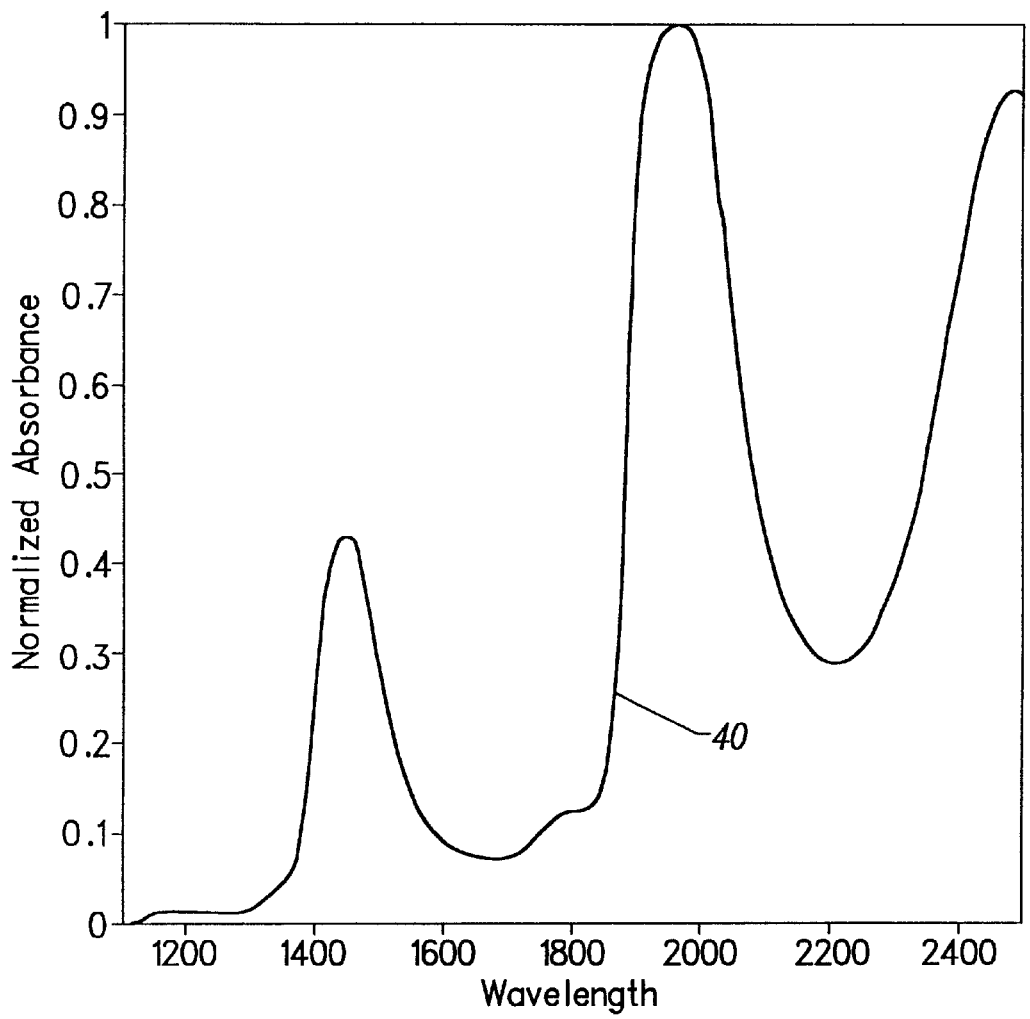
FIG. 3 shows a normalized NIR absorbance spectrum of water.
Figure 4:
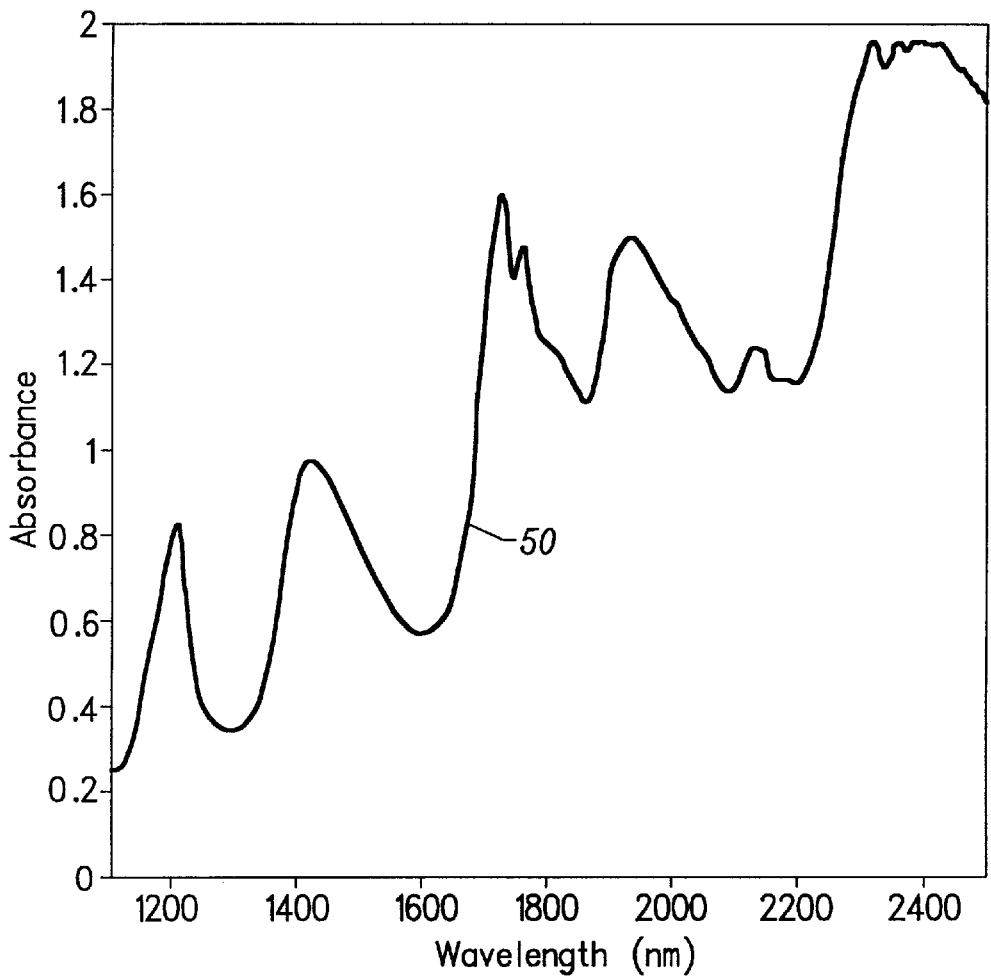
FIG. 4 shows a NIR absorbance spectrum of an excised sample of animal fat.

For the purpose of feature extraction and classification, a two-component basis set was provided using the fundamental absorbing components of skin, water and fat. First, water was scanned through a 1 mm cuvette using a spectrometer according to the preferred embodiment, as described previously. The absorbance spectrum 40, shown in FIG. 3, was calculated through $-\log(T/T_0)$ where T is the reflected light and $T_0$ is the light incident on the sample determined by scanning a blank. A pure component absorbance spectrum of fat 50 was measured by scanning excised bovine adipose tissue with a spectrometer according to the preferred embodiment. The resulting spectrum is shown in FIG. 4.

Experimental Data Set

The Experimental Data Set for calibrating the models described subsequently was realized through a study of nineteen volunteers (sixteen male and three female) with ages ranging from 21 to 55 years. One absorbance spectrum was measured on each subject's forearm on two successive days with a spectrometer according to the preferred embodiment. The percent body fat of the participants was estimated through the Siri equation for body composition (See W. Siri, *The gross composition of the body*, Adv. Biol. Med. Phys., vol. 4, pp. 239–280 (1956). Skin fold thickness was measured on the biceps, triceps, subscapular and suprailiac regions of each subject with a pair of research grade calipers of the type known as HARPENDEN, manufactured by British Indicators, LTD.

While this is a specific experiment aimed at the determination of a suitable set for classification and estimation of features and attributes associated with the thickness of adipose tissue, one skilled in the art will readily appreciate that, for different subjects and for different target performance levels, other experiments with more or fewer subjects would be performed.

Projection algorithm

Figure 5:
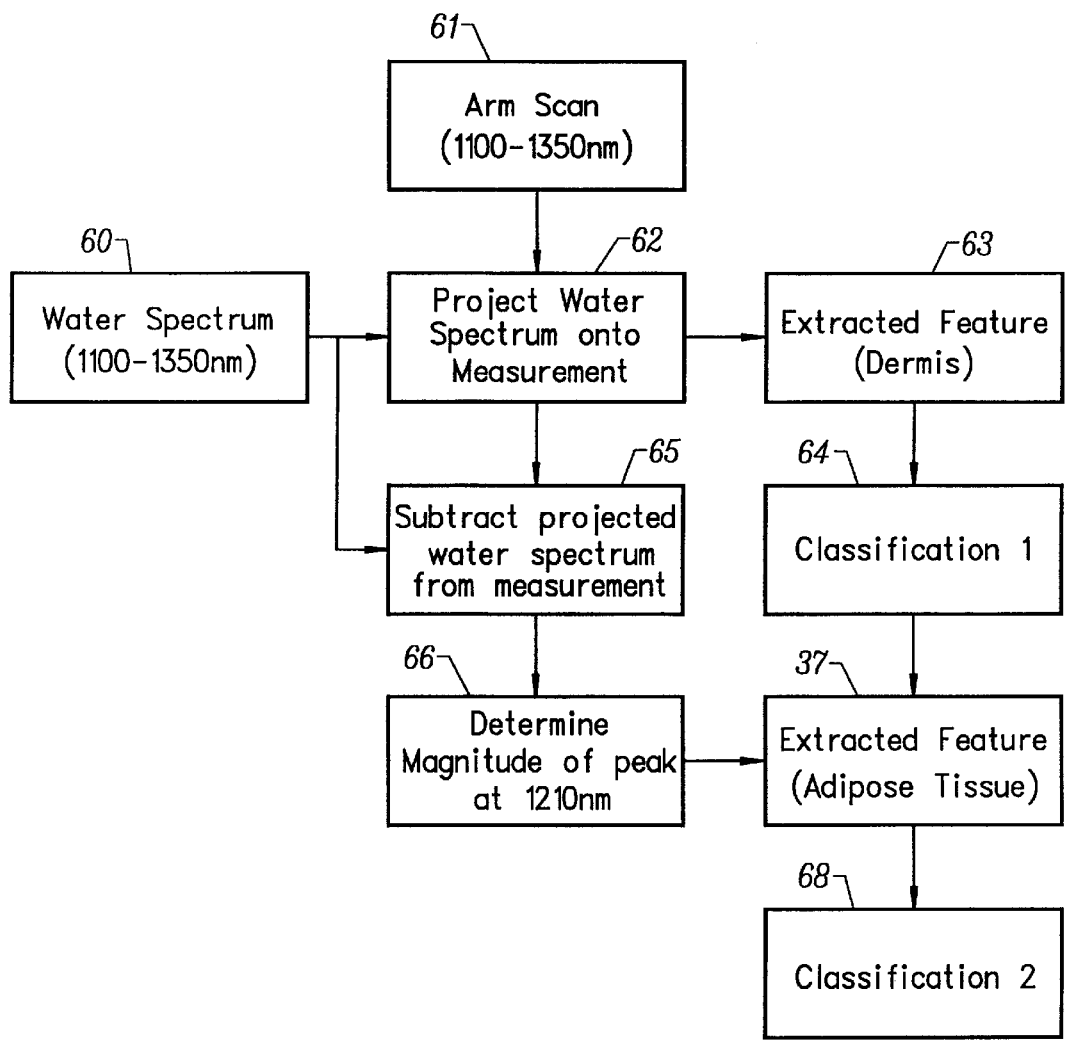
FIG. 5 provides a block diagram of a procedure for extracting spectral features related to the dermis and adipose tissue according to the invention.

A first method of feature extraction characterizes tissue based on an absorbance spectrum measured with a near-IR spectrometer in the wavelength region of 1100–1350 nm. Referring now to FIG. 5, the measured spectrum 61 is normalized by projecting 62 a water absorbance spectrum 60 onto the measured spectrum 61 and calculating the difference 65. The peak 66 of the resulting fat absorbance band near 1210 nm is used to determine the percent body fat or thickness of adipose tissue at the measurement site using a simple univariate mapping.

Given the measured spectrum 61, x, and the pure component spectrum of water 60, p, the projection 62 of the water spectrum onto the measured spectrum is determined according to $$m = [p_w p_w^T]^{-1} p_w x_w \quad (11)$$

where m is a scalar representing the magnitude of water absorbance and the subscript w represents a subset of wavelengths (1100–1150 nm and 1300–1350 nm). Since water is predominantly concentrated in the dermal layer, the magnitude of m represents an extracted feature 63 related to the characteristics of the dermis that may be subsequently used in the classification 64 of subjects through linear discriminant analysis as described below.

Figure 6:
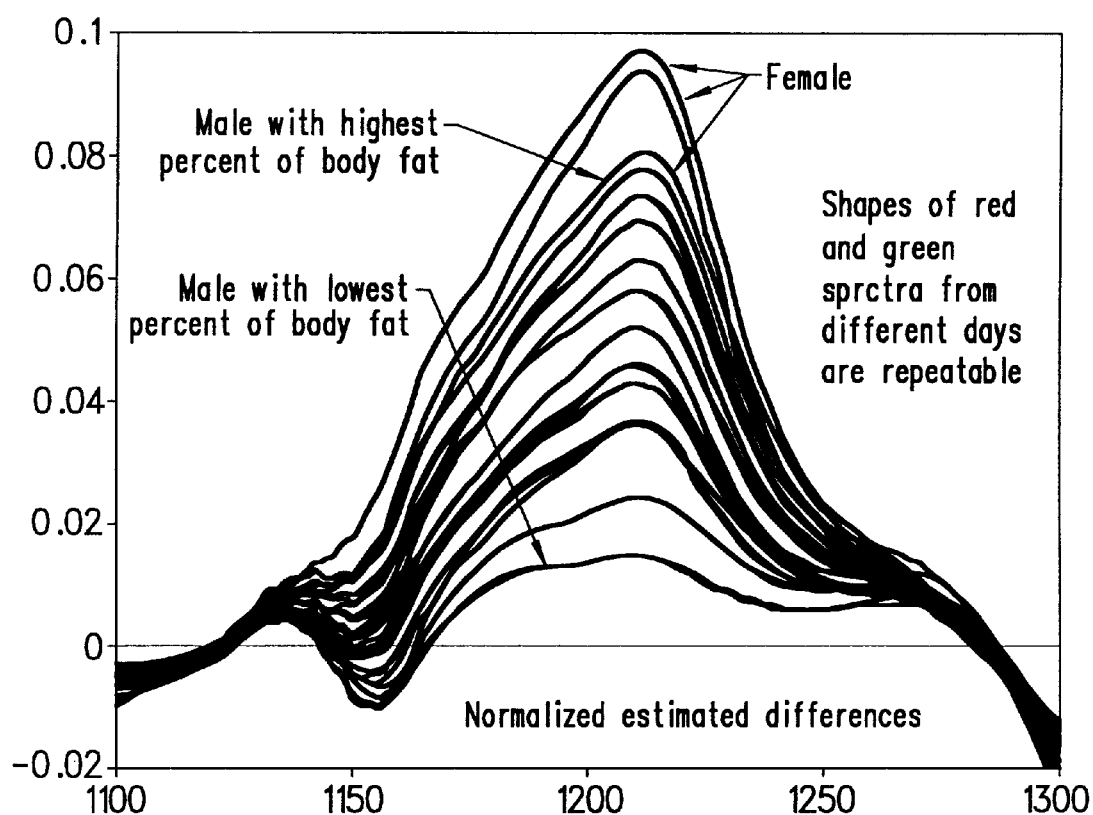
FIG. 6 shows the NIR absorbance spectra of 19 subjects normalized according to the procedure of FIG. 5 according to the invention.

The water spectrum 60 is projected 62 and subtracted 65 from the measurement 61 according to $$z = x - mp \quad (12)$$

where z is the final spectrum. The method summarized in equations 11 and 12, above was applied to the Experimental Data Set and plots of z for all subjects in the Experimental Data Set are shown in FIG. 6. As the figure cleary shows, the magnitude of the absorbance peak at 1210 nm correlates with percent body fat, so that individuals with the highest percent body fat have the most pronounced absorbance peak at or around 1210 nm. Furthermore, the magnitude of this peak is a feature 67 related to the thickness of the adipose tissue in the subcutaneous layer that is used in a further classification 68 of subjects.

While this procedure was explained through example in the 1100–1350 nm range, one skilled in the art will appreciate that this method is easily extendable to the 1650–1800 nm wavelength range where additional features related to the absorbance of adipose tissue exist at 1720 and 1760 nm as shown in FIG. 1. Furthermore, the basis set could include other components that could then be used in the projection to extract features related to other characteristics of the tissue including hydration, protein concentrations, skin cholesterol, and others.

For classification, a Discriminant function is applied to classify the subjects based on the two features 63, 67, either in two separate steps 64, 68 as indicted in FIG. 5, or through a single step. For example, given the vector f containing both features 63,67 of FIG. 5, the subject is classified into one of two categories to produce the scalar, L:

$$L = fw \quad (13)$$

where w is a vector of weights. This result is compared to $\overline{L}$, the center between the two classes. If $L > \overline{L}$ then the subject is classified into Group 1. If not, the spectrum is classified as belonging to Group 2. The two resulting groups contain a greater degree of homogeneity in the sampled tissue volume than the original population.

In addition, an arbitrary number of groups can be defined, depending upon the desired level of homogeneity in each group. Furthermore, a fuzzy classification system can be developed by defining a set of membership functions for the set of predefined classes. For example, given z, the peak magnitude of the spectra in FIG. 6, the group of subjects may be denoted as thin, medium and fat corresponding to the absorbance related to fat in adipose tissue. For each class the mean feature, $\overline{z}$, and standard deviation, $\sigma$, are calculated. The membership function defining the degree of membership in a particular class is given by $$y = e^{\frac{-1}{2\sigma^2}(z-\overline{z})^2} \quad (14)$$

where y is the degree of membership. While this membership function is Gaussian, one skilled in the art will appreciate that the suitable membership function is specific to the application. The mean and standard deviation associated with each of the three categories were determined based on the target population in the Experimental Data Set.

Values for the feature inputs to the membership functions that are unusually high or low fall outside the expected range of the sub-sets and are assigned low membership values. This information is used to indicate that the subject's tissue characteristics are outside of the previously examined population and is used for outlier analysis. For the current implementation when y<0.1 for all sub-sets the prediction is assigned a low confidence level.

The resulting class memberships are suitable for use in categorization for blood analyte prediction as described by Malin, et al in a related application Ser. No. 09/359,191. The membership functions described have been designed for a specific population of subjects and cannot be generalized to all potential individuals. The invention, however, is directed to the arbitrary use of membership functions to assign a degree of membership in a given class to a subject for blood analyte prediction.

Estimation of Body Composition

Figure 7:
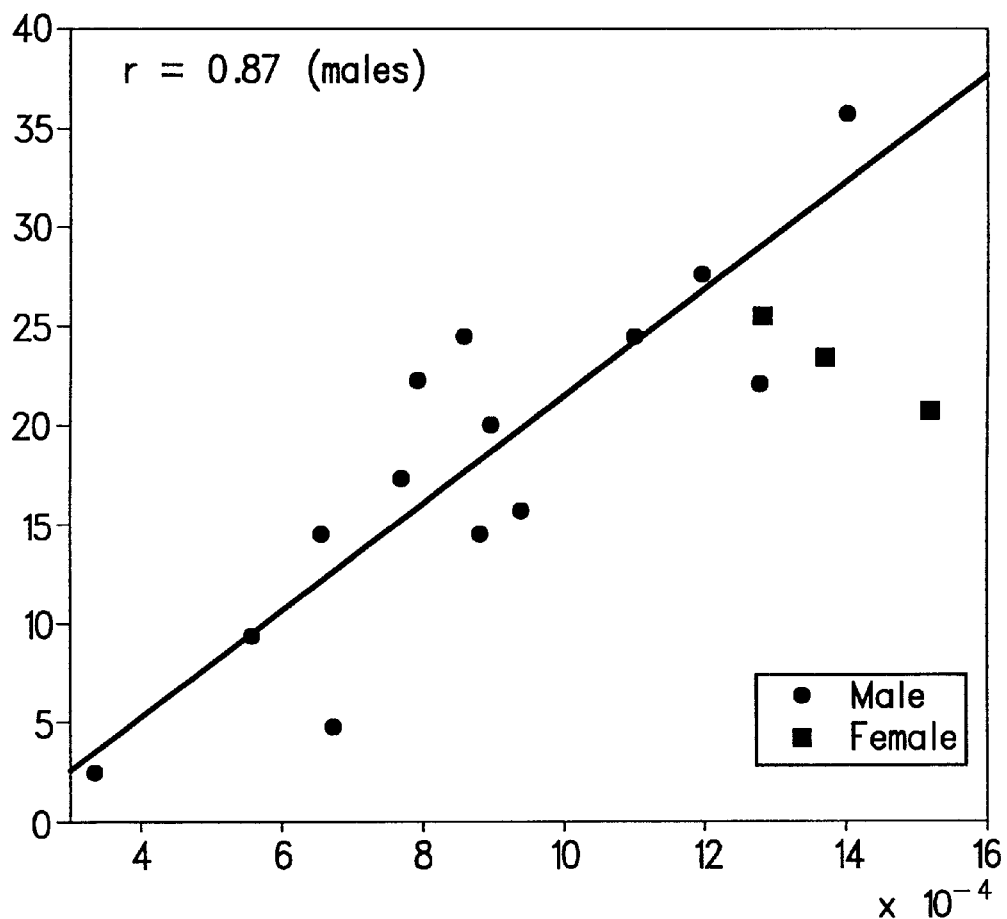
FIG. 7 shows a plot of a single wavelength calibration for body fat according to the invention.

The procedure for extracting features related to the fat in adipose tissue shown in FIG. 5 can be used to estimate the percent body fat of the individual. For example, the extracted feature, z, at 1210 nm was plotted versus percent body fat in FIG. 7. The percent body fat is estimated via $$\text{fat \%} = az_{1210nm} + b \qquad (15)$$

where a is the slope of the line in FIG. 7 and b is the corresponding intercept, and $z_{1210nm}$ is the magnitude of z at 1210 nm. In this particular example, one calibration was developed for all subjects regardless of age or sex. Improved accuracy can be obtained through a larger data set and the use of age and sex estimates as indicated by Equation 10.

Feature Extraction with Two or Three Wavelengths

Figure 8:
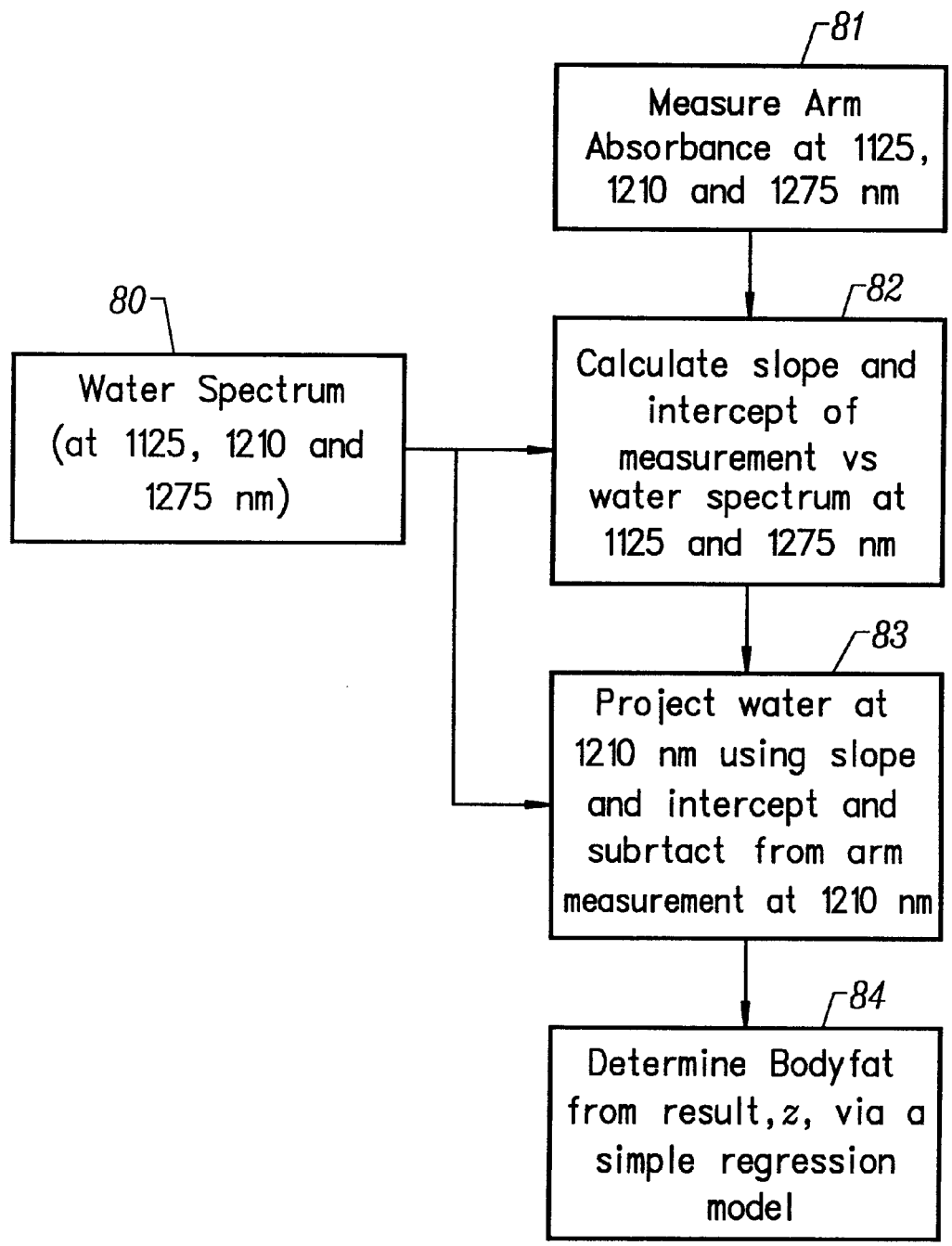
FIG. 8 provides a block diagram of a procedure for measuring body fat via three wavelengths according to the invention.

The method of feature extraction and body fat estimation described above can be performed with an entire spectrum as previously described or with 2–3 wavelengths, depending on the desired level of accuracy. For example, the procedure of FIG. 5 was modified as shown in FIG. 8 and involves the measurement of body fat using spectra 81 measured at three wavelengths. The feature z, is calculated by projecting the water spectrum 80 on the measurement at only two wavelengths 82 and determining the difference 83 at a third wavelength. Therefore, the procedure can be implemented in a system with three LED's equally spaced about a single detector or a near-infrared spectrometer.

The selected wavelengths are preferably 1124, 1210 and 1276 nm and the corresponding absorbances of water are 0.4781, 0.184148 and 0.164745 respectively. The percent body fat is estimated 84 via $$\text{fat \%} = az_{1210nm} + b \qquad (16)$$

where a is the slope, b is the intercept, and $z_{1210nm}$ is the magnitude of z at 1210 nm (the extracted feature). In the current embodiment a=388.18 and b=9.177.

Figure 9:
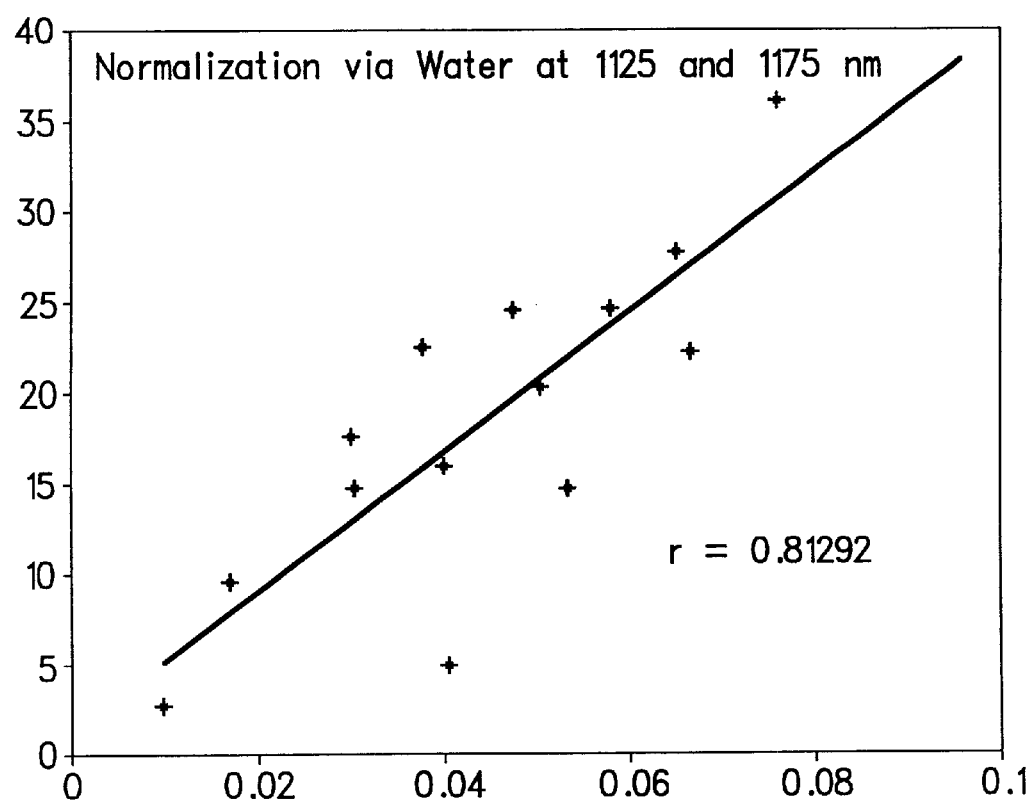
FIG. 9 shows a plot of actual body fat versus the extracted feature of FIG. 7 according to the invention.

This procedure was applied to the Experimental Data Set and the extracted feature, $z_{1210nm}$, was calculated for each absorbance spectrum 81. The actual percent body fat of each subject versus the extracted feature is shown in FIG. 9. The correlation coefficient (r) of 0.81 indicates that the same method can be generalized to involve two or more wavelengths.

Abstract Feature Extraction

Figure 10:
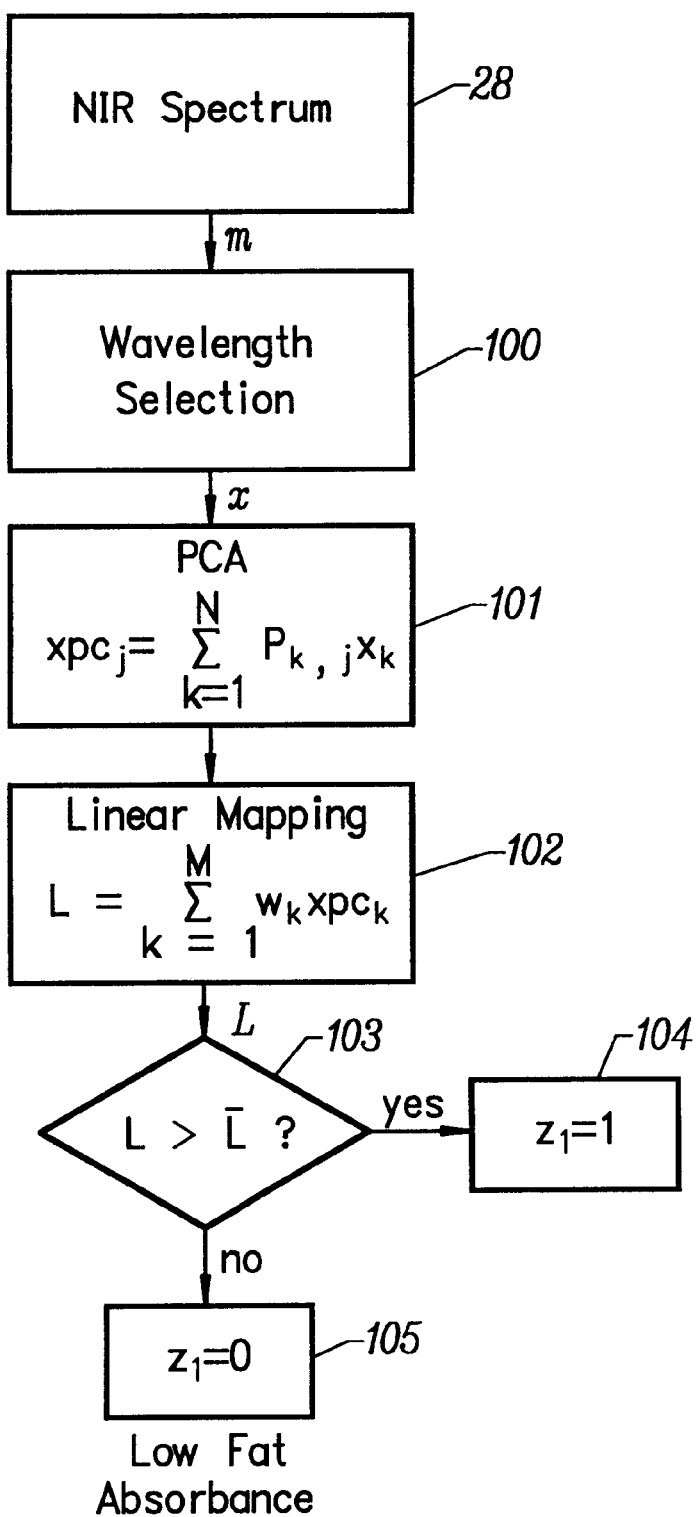
FIG. 10 shows a block diagram of a method of abstract feature extraction and subject classification according to the invention.
Figure 11:
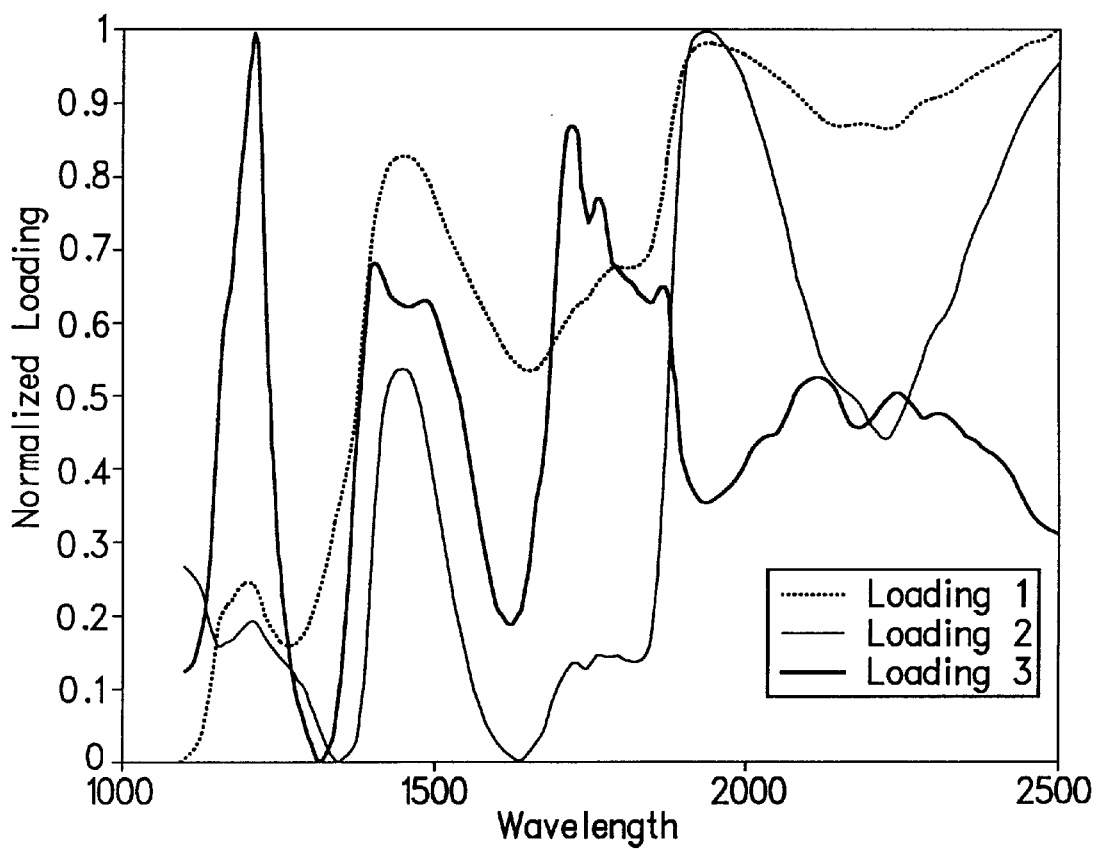
FIG. 11 shows a plot of the first three eigenvectors of a principle component analysis of a dataset following the feature extraction procedure of FIG. 10 according to the invention.
Figure 12:
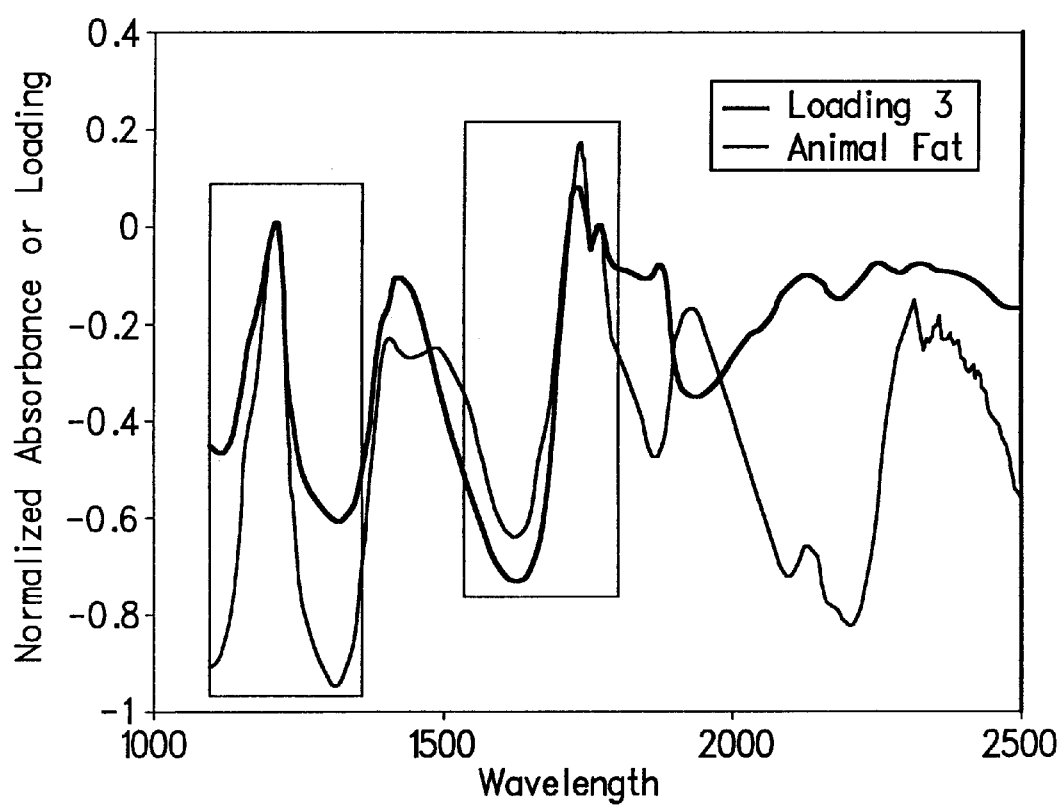
FIG. 12 is a comparison of the third loading (eigenvector) of FIG. 11 with the animal fat spectrum of FIG. 4 according to the invention.

Abstract feature extraction is used as an alternate method for feature extraction and subject classification as depicted in FIG. 10. For this implementation, a separate data set of 266 arm scans on subjects of diverse sex, age and ethnicity were used to determine the parameters. A principal component analysis was performed on the 266 sample data set and the scores of the first three eigenvectors are plotted in FIG. 11. FIG. 12 compares the third eigenvector from FIG. 11 with the absorbance spectrum of the animal fat sample of FIG. 4. As shown, the third eigenvector closely matches the absorbance spectrum of fat. Therefore, the first three scores, $xpc_{1-3}$, are used as features for subject classification.

The determination of the subject class occurs as follows. First, the absorbance spectrum, m 28, is provided from the outlier detection system. Wavelength selection 100 is applied to truncate the spectral range to regions with significant absorbance due to fat in adipose tissue (1100 to 2500 nm). The spectrum is projected 101 onto the eigenvectors, $p_k$, previously developed through a principal component analysis on the 266 sample calibration set. The calculation, shown in FIG. 10, produces the 1 by N vector of scores, xpc.

A Discriminant function is applied to classify the subjects on the basis of the first M scores (M=3 in this application). The scores are rotated 102 through a cross product with the discriminant w, as depicted in FIG. 10 to produce the scalar, L. This result is compared 103 to $\overline{L}$, the center between the two classes. If $L > \overline{L}$ then the sampled tissue volume is classified as having significant absorbance due to fat 104. If not, the tissue volume is classified as having low absorbance due to fat 105. As discussed previously, one skilled in the art will recognize that this system can be generalized to an arbitrary number of classes or employ a fuzzy classification system.

General Estimation and Classification Methods

Figure 13A:
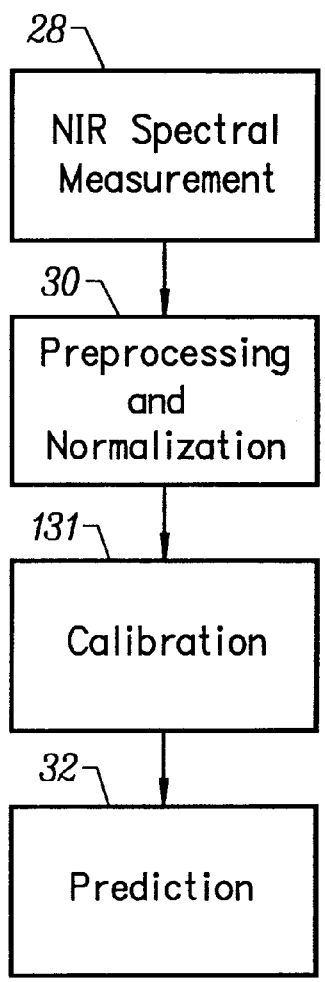
FIG. 13 provides a pair of block diagrams showing generalized procedures for body fat prediction and classification of subjects according to spectral features associated with body fat respectively, according to the invention.
Figure 14:
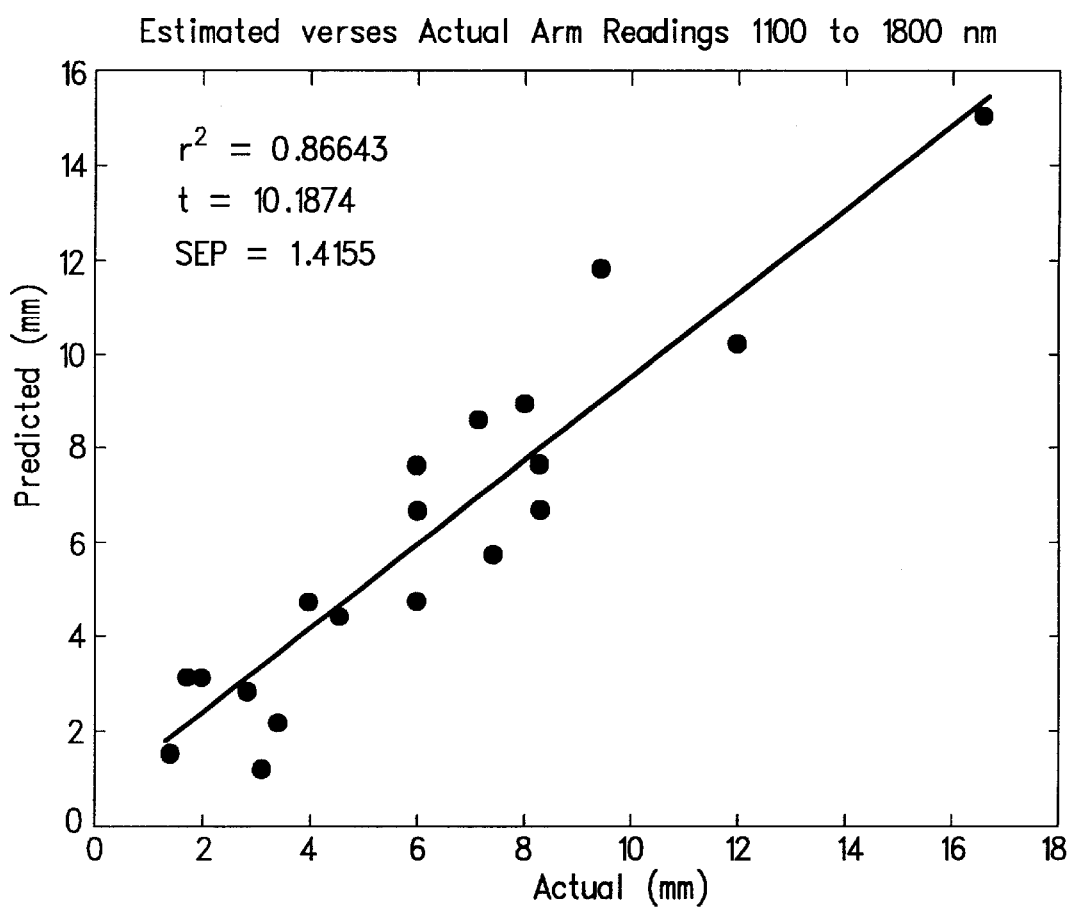
FIG. 14 shows a plot of predicted skin fold thickness versus actual skin fold thickness according to the invention.

The general estimation implementation, shown in FIGS. 13a, uses a general calibration model 131 to predict a variable related to the absorbance of fat in adipose tissue at one or more wavelength regions from 1100–2500 nm. An absorbance spectrum 28 is provided. Specific wavelength ranges, such as 1550 to 1800 nm and 2050 to 2350 nm, are selected and preprocessed 30 using windowed multiplicative scatter correction or other appropriate methods. The processed data are mapped to a body fat prediction 32 using a calibration model 131 that is realized using known methods, including principal component regression: (See H. Martens, T. Naes. *Multivariate Calibration,* New York: John Wiley and Sons, (1989), partial least squares regression and artificial neural networks. For example, a five-factor partial-least squares model was developed for estimating the skin fold thickness using spectra from the Experimental Data Set. The test set predictions through cross validation are shown in FIG. 14. As shown in the figure the standard error of prediction (SEP) was 1.42, resulting in a prediction accuracy of approximately seventy percent. While the experimental results demonstrate the validity and benefit of the estimation procedure, accuracy of the results is directly dependent on the accuracy of the spectral measurements. Further improvement to results accuracy will be achieved through improvements in the noise level and the resolution of the spectrometer.

Figure 13B:
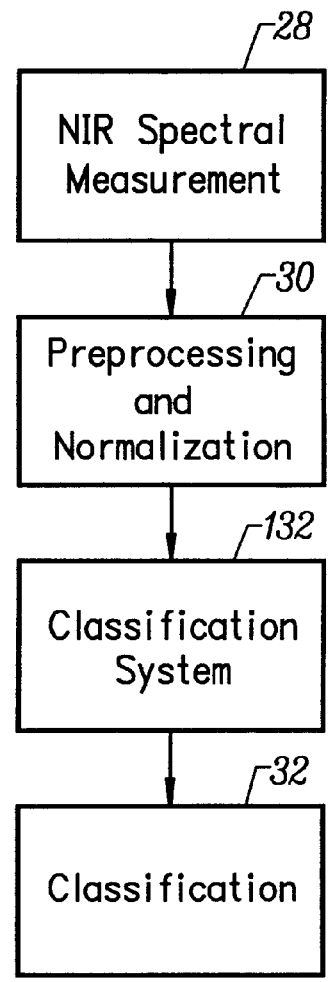

The general classification procedure for grouping subjects according to features related to the absorbance of fat in adipose tissue is shown in FIG. 13b. Again an absorbance spectrum 28 is provided. Specific wavelength ranges, such as 1100–1350 nm and 1550 to 1800 nm, are selected and preprocessed 30 using windowed multiplicative scatter correction or other appropriate methods. The processed data are subjected to feature extraction through a factor-based method, such as principal component analysis. Finally, the subject is classified into a body fat category 32 through a classification procedure 132, such as linear Discriminant analysis, SIMCA, k nearest-neighbor and various forms of artificial neural networks.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

What is claimed is:

1. A non-invasive method of characterizing and classifying the state and structure of tissue on the basis of spectral absorbance features related to fat in the subcutaneous tissue comprising the steps of:
   providing a calibration set of exemplary measurements;
   measuring NIR absorbance spectrum of a skin tissue sample;
   detecting outliers, wherein said outliers are invalid measurements caused by spectral variation due to any of instrument malfunction poor sampling and subjects outside of said calibration set;
   preprocessing said NIR spectrum, wherein said preprocessing step includes one or more transformations that attenuate noise and instrumental variation without affecting signal of interest, including any of wavelength selection, scaling, normalization, smoothing, derivatives, and filtering;
   providing a basis set, wherein said basis set comprises a pure component spectrum of water and one of animal fat, for feature extraction and preprocessing; and
   extracting features, whereby features of measurements relevant to classification are determined.

2. The method of claim 1, wherein said spectrum is denoted by a vector $m \in R^N$ of absorbance values pertaining to a set of N wavelengths $\lambda \in R^N$.

3. The method of claim 1, wherein said NIR spectral measurements are in the wavelength region of approximately 1100 to 2500 nm.

4. The method of claim 1, wherein said outlier detection step employs principal components analysis, and residual analysis to detect spectral outliers.

5. The method of claim 4, wherein said outlier detection step further comprises the steps of:
   projecting a spectrum m onto a plurality of eigenvectors, contained in a matrix o, said matrix o being previously developed through principal components analysis of said calibration set, where $$xpc_o = \sum_{k=1}^{7} mo_k,$$

and where $o_k$ is the $k^{th}$ column of the matrix o;
   determining the residual q, according to $$q = m - xpc_o o^T;$$

comparing said residual q to three times the standard deviation of the residual of said calibration set; and
   reporting said sample as an outlier if q is greater.

6. The method of claim 4, wherein said feature extraction step comprises principal component analysis.

7. The method of claim 6, wherein said feature extraction step comprises the steps of:
   truncating said spectrum m at the wavelength region of approximately 1100–2500 nm;
   projecting said truncated spectrum onto a plurality, $p_k$, of eigenvectors, where said eigenvectors were previously calculated through principal component analysis of said calibration set;
   wherein said projection produces a 1 by N vector of scores, xpc; and
   applying a Discriminant function whereby said samples are classified on the basis of the first M scores, wherein said scores are rotated through a cross product with a Discriminant, w, to produce a scalar, L.

8. The method of claim 7, wherein M=3.

9. The method of claim 1, wherein said feature extraction step comprises any mathematical transformation that enhances a quality or aspect of sample measurement for interpretation to represent concisely properties and characteristics of the tissue measurement site.

10. The method of claim 9, wherein said feature extraction step comprises normalizing the magnitude of absorbance bands of fat in adipose tissue.

11. The method of claim 9, wherein said feature extraction step comprises comparing water and fat absorbance spectra of said sample to water and fat absorbance spectra of said calibration set.

12. The method of claim 9, wherein said features are represented in a vector $z \in R^M$ that is determined from a preprocessed measurement through:

$$z = f(\vec{e}, x),$$

where $F: R^N \to R^M$ is a mapping from a measurement space to a feature space, wherein decomposing $f(.)$ yields specific transformations, $f_i(.)$: $R^N \to R^{M_i}$, for determining a specific feature, wherein the dimension $M_i$ indicates whether an $i^{th}$ feature is a scalar or vector and an aggregation of all features is the vector z, and wherein a feature exhibits a certain structure indicative of an underlying physical phenomenon when said feature is represented as a vector or a pattern.

13. The method of claim 12, wherein individual features are divided into two categories comprising:
   abstract features that do not necessarily have a specific interpretation related to a physical system; and
   simple features that are derived from an a priori understanding of a sample and that can be related directly to a physical phenomenon.

14. The method of claim 1, further comprising the step of:
   classifying said sample according to predefined categories of fatness and leanness.

15. The method of claim 14, wherein said spectrum is limited to any of the wavelength regions of approximately 1100–1350 nm and approximately 1650–1800 nm.

16. The method of claim 15, wherein said feature extraction step comprises the step of:
   normalizing said limited spectrum.

17. The method of claim 16, wherein said normalizing step comprise the steps of:
   projecting said spectrum of water on said limited spectrum according to $$m = [p_w p_w^T]^{-1} p_w x_w,$$

where m is a scalar representing the magnitude of water absorbance and the subscript w represents a subset of wavelengths; and
   subtracting said pure water spectrum from said limited spectrum according to $$z = x - mp,$$

where z is a final spectrum.

18. The method of claim 17, wherein class membership is defined by a continuum of grades, and wherein a set of membership functions map a feature space into an interval [0,1] for each class and wherein an assigned grade of "1" represents a highest degree of class membership.

19. The method of claim 18, wherein the mapping from the feature space to a vector of class memberships is given by:

$$c_k = f_k(z),$$

where k=1, 2, ... P, and where $f_k(.)$ is the membership of the $K^{th}$ class, and where $c_k \in [0,1]$ for all k and where a vector $c \in R^P$ is the set of all class memberships.

20. The method of claim 19, wherein a membership function is represented by $$y = e^{\frac{-1}{2\sigma^2}(z-\bar{z})^2},$$

where y is the degree of membership in a fuzzy subset, z is the feature used to determine membership, $\bar{z}$ is the center of a fuzzy subset, and $\sigma$ is the standard deviation.

21. The method of claim 19, wherein said membership vector provides the degree of class membership in each of said predefined classes.

22. The method of claim 14, wherein said classification step comprises the steps of:
measuring similarity of at least one feature to said predefined categories; and
assigning membership in said predefined categories.

23. The method of claim 22, wherein said assigning step uses mutually exclusive classes and assigns each sample to one class.

24. The method of claim 23, wherein said assigning step further comprises the steps of:
mapping said sample to one of said predefined classes;
applying a decision rule to assign class membership.

25. The method of claim 24, wherein said mapping step is given by:

$$L = f(z),$$

where L is a scalar that measures distance of a sample from the predefined categories.

26. The method of claim 24, wherein limits for said mapping and said decision rule are determined from a calibration set of exemplary measurements and corresponding reference values of fat and lean through a classification calibration procedure.

27. The method of claim 26, wherein said classification calibration comprises any of linear Discriminant Analysis, SIMCA, k nearest neighbor, fuzzy classification artificial neural networks.

28. The method of claim 27, wherein said mapping step is given by $$L = fw,$$

where w is a vector of weights, and wherein L is compared with $\bar{L}$, where $\bar{L}$ is a center between two of said mutually exclusive classes.

29. The method of claim 28, wherein said assigning step employs a decision rule, wherein said decision rule is
If $L > \bar{L}$, said sample is assigned to a first of said two classes;
If $L \leq \bar{L}$, said sample is assigned to a second of said two classes.

30. The method of claim 23, wherein said categories are "fat" and "lean" and where $L_{fat}$ corresponds to a representative value for said "fat" class and $L_{lean}$ corresponds to a representative value for said "lean" class; and wherein said class assignment is based on the closeness of L to $L_{fat}$ and $L_{lean}$.

31. The method of claim 30, wherein a distance $d_{fat}$ of L to $L_{fat}$ is measured by $$d_{fat} = |L_{fat} - L|,$$

and wherein a distance $d_{lean}$ of L to $L_{lean}$ is measured by $$d_{lean} = |L_{lean} - L|.$$

32. The method of claim 3, wherein said decision rule is:
If $d_{lean} < d_{fat}$, said sample is classified as "lean;"
If $d_{lean} \geq d_{fat}$, said sample is classified as "fat."

33. The method of claim 22, wherein said assigning step uses a fuzzy classification system that allows class membership in more than one class simultaneously.

34. The method of claim 1, further comprising the step of:
estimating the thickness of a skinfold, said skinfold comprising a layer of adipose tissue.

35. The method of claim 34, wherein said estimating step uses any of preprocessed spectra and extracted features.

36. The method of claim 35, wherein said estimating step further comprises the step of:
providing a calibration model to map said preprocessed spectrum through a mapping to an estimate of skin fold thickness.

37. The method of claim 36, wherein said mapping is linear.

38. The method of claim 37, wherein said skin fold thickness estimate is determined according to $$\hat{y} = \sum_{k=1}^{N} w_{c,k} x_k;$$

given the preprocessed spectrum x, and the calibration model $w_c$, where $w_{c,k}$ is the $k^{th}$ element of $w_c$ and $\hat{y}$ is the skin fold thickness estimate.

39. The method of claim 38, wherein said calibration model employs factor analysis to decompose a high-dimensional (redundant) data set comprising absorbance, intensity or reflectance measurements at a plurality of wavelengths to significant factors representing the majority of variation within said data set; and
wherein said calibration model includes factors that capture variation in said spectra correlated with variation in skin fold thickness.

40. The method of claim 39, further comprising the steps of;
projecting said samples into a resulting factor space to produce a set of scores for each sample; and
applying multiple linear regression to model the relationship between said scores and said skin fold thickness.

41. The method of claim 36, wherein said mapping is non-linear.

42. The method of claim 41, wherein said non-linear mapping is specified through any of artificial neural networks and non-linear partial least squares regression.

43. The method of claim 34, further comprising the step of:
estimating the body composition of a subject.

44. The method of claim 43, wherein said body composition estimating step comprises the step of;
mapping a skin fold thickness estimate, a sex estimate and an age estimate to an estimate of the percent body fat of said subject according to:

$$y = f(x_1, x_2, x_3)$$

where y is the estimate of the percent body fat, $x_1$ is the skin fold thickness estimate, $x_2$ is the sex estimate, and $x_3$ is the age estimate and f( ) is a calibration model.

45. The method of claim 44, wherein said model f( ) is determined by applying a nonlinear regression method to a calibration set of exemplary measurements.

46. The method of claim 43, wherein said spectrum is limited to three wavelengths.

47. The method of claim 46, wherein said three wavelengths are 1124, 1210, and 1276 nm.

48. The method of claim 47, wherein said feature extraction step comprises the step of:

normalizing said limited spectrum.

49. The method of claim 48, wherein said normalizing step comprises the steps of:

projecting said spectrum of water onto two of said three wavelengths; and subtracting said pure water spectrum from said limited spectrum at the third of said wavelengths according to $$z = x - mp,$$

where z is a final spectrum.

50. The method of claim 48, further comprising the step of:

estimating the percent bodyfat according to $$\text{fat } \% = az_{1210nm} + b,$$

where a is the slope, b is the intercept and $z_{1210nm}$ is the magnitude of z at 1210 nm, where z is an extracted feature.

51. The method of claim 34, further comprising the step of:

performing a blood analyte prediction.

52. An apparatus for non-invasively characterizing and classifying the state and structure of a skin tissue sample based on spectral absorbance features related to the absorbance of fat in the subcutaneous tissue of a subject comprising:

means for generating near (NIR) energy;

means for separating said generated NIR energy into a plurality of wavelength regions;

an optical interface comprising:

means for transmitting said NIR energy from said wavelength separating means towards a target measurement site on a subject; and means for collecting NIR energy emanating from said measurement site;

means for detecting said collected energy and converting said collected energy to a voltage;

means for converting said voltage to a digital value; and means for analyzing said digital value whereby said analysis results in any of a characterization and a classification of said skin tissue sample.

53. The apparatus of claim 52, wherein said energy source and said wavelength separating means together comprise an array of LED's surrounding said detecting means in a radial fashion, each of said LED's and said detecting means having a lateral edge and wherein each of said LED's successively emits energy at a specific wavelength in a set of pre-selected wavelengths.

54. The apparatus of claim 53, wherein said set of pre-selected wavelengths includes 1100 nm, 1208 nm, 1210 nm, 1275 nm, 1350 nm, 1650 nm, 1720 nm, 1760 nm.

55. The apparatus of claim 53, wherein said lateral edge of any of said LED's comprises a point of illumination and said lateral edge of said detecting means comprises a point of detection, and wherein a distance between said point of illumination and said point of detection is approximately 1–3 mm.

56. The apparatus of claim 55, wherein said LED array and said detecting means are coupled with said measurement site by means of staring optics and a lens system.

57. The apparatus of claim 52, wherein said energy source is a quartz halogen lamp wherein said lamp transmits energy in the wavelength range of approximately 1100–2500 nm.

58. The apparatus of claim 57, wherein said wavelength separating means is any of a monochromator and an interferometer.

59. The apparatus of claim 52 wherein said transmission means is any of a light pipe, a fiber-optic probe, a lens system, and a light-directing mirror system.

60. The apparatus of claim 59, wherein a point of illumination is set through any of a focusing lens and a fiber-optic probe.

61. The apparatus of claim 52, wherein said energy detecting means comprises InGaAs detectors.

62. The apparatus of claim 52, wherein said digitizing means is a 16-bit A/D converter.

63. The apparatus of claim 52, wherein said energy collecting means comprises any of at least one staring optical detector and at least one fiber-optic probe.

64. The apparatus of claim 60, wherein a point of detection is set through any of a staring optical detector or a fiber-optic probe.

65. The apparatus of claim 52, wherein said means for analysis comprises a digital processor programmed to perform a tissue characterization procedure;

wherein said digital value is processed by said relative age estimation procedure and whereby said tissue sample is characterized.

* * * * *